(12) United States Patent
Conley

(10) Patent No.: US 12,144,688 B2
(45) Date of Patent: Nov. 19, 2024

(54) CANNULATED SCREW LENGTH MEASUREMENT GAUGE

(71) Applicant: Acumed LLC, Hillsboro, OR (US)

(72) Inventor: Brian Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 181 days.

(21) Appl. No.: 17/483,979

(22) Filed: Sep. 24, 2021

(65) Prior Publication Data

US 2022/0104902 A1 Apr. 7, 2022

Related U.S. Application Data

(60) Provisional application No. 63/086,773, filed on Oct. 2, 2020.

(51) Int. Cl.
*A61B 90/00* (2016.01)
*A61B 17/86* (2006.01)

(52) U.S. Cl.
CPC ............ *A61B 90/06* (2016.02); *A61B 17/864* (2013.01); *A61B 2090/062* (2016.02)

(58) Field of Classification Search
CPC ........ A61B 2090/061; A61B 2090/062; A61B 17/864; A61B 90/06
See application file for complete search history.

(56) References Cited

U.S. PATENT DOCUMENTS 5,122,146 A * 6/1992 Chapman ............ A61B 17/921
606/67
5,431,639 A 7/1995 Shaw
(Continued)

FOREIGN PATENT DOCUMENTS

DE 4016476 C2 * 4/1994 ............ A61B 90/06
KR 102105411 B1 4/2020
(Continued)

OTHER PUBLICATIONS

International Search Report corresponding to related International Patent Application No. PCT/US2021/051891 mailed Dec. 27, 2021, 3 pages.
(Continued)

*Primary Examiner* — Kevin T Truong
*Assistant Examiner* — Diana Jones
(74) *Attorney, Agent, or Firm* — K&L Gates LLP

(57) ABSTRACT

The presently disclosed depth gauge device includes a tube with a measurement rod inserted into one end of the tube. The measurement rod includes a set of indicators associated with length values. A surgeon may translate the provided depth gauge device over a guidewire, which causes the guidewire to force the measurement rod partially out of the tube. Once the depth gauge device contacts bone, the indicator on the measurement rod that lines up with a designated spot on the tube indicates a guidewire depth into bone, which is equal to a screw length that is needed for the procedure. Additionally, the provided depth gauge device is constructed such that the measurement rod maintains its positioning in the absence of applied force. This enables a surgeon to remove the depth gauge device from the bone or completely from the guidewire when obtaining a measurement reading.

7 Claims, 7 Drawing Sheets

(56) References Cited

U.S. PATENT DOCUMENTS

| | | | |
|---|---|---|---|
| 2005/0187560 A1* | 8/2005 | Dietzel | A61B 17/155 606/102 |
| 2009/0054906 A1 | 2/2009 | Walthall et al. | |
| 2009/0228015 A1* | 9/2009 | Ellis | A61B 5/1076 606/86 R |
| 2012/0010619 A1* | 1/2012 | Barsoum | A61B 17/8897 606/86 R |
| 2012/0109132 A1* | 5/2012 | Ellis | A61B 5/1076 606/80 |
| 2013/0012942 A1 | 1/2013 | Nelson et al. | |
| 2013/0304068 A1* | 11/2013 | Larche | A61B 17/8875 606/79 |
| 2014/0276884 A1* | 9/2014 | Lizardi | A61B 90/00 606/102 |
| 2014/0296861 A1* | 10/2014 | McCarthy | A61B 90/06 606/96 |
| 2015/0133944 A1 | 5/2015 | Kortenbach | |
| 2015/0196340 A1* | 7/2015 | Combrowski | A61B 17/88 606/104 |
| 2017/0189036 A1* | 7/2017 | Rajeev | A61B 90/03 |
| 2018/0028214 A1* | 2/2018 | Friedman | A61B 17/3213 |

FOREIGN PATENT DOCUMENTS

| | | | | |
|---|---|---|---|---|
| WO | WO-2011116208 A1 * | 9/2011 | | A61B 17/1764 |
| WO | WO-2019197957 A1 * | 10/2019 | | A61B 17/3472 |
| WO | 2020092951 A2 | 5/2020 | | |

OTHER PUBLICATIONS

International Written Opinion corresponding to related International Patent Application No. PCT/US2021/051891 mailed Dec. 27, 2021, 8 pages.

International Preliminary Report corresponding to related International Patent Application No. PCT/US2021/051891 mailed Apr. 13, 2023, 10 pages.

Extended European Search Report corresponding to related European Patent Application No. 21876241.7 dated Oct. 9, 2024, 9 pages.

* cited by examiner

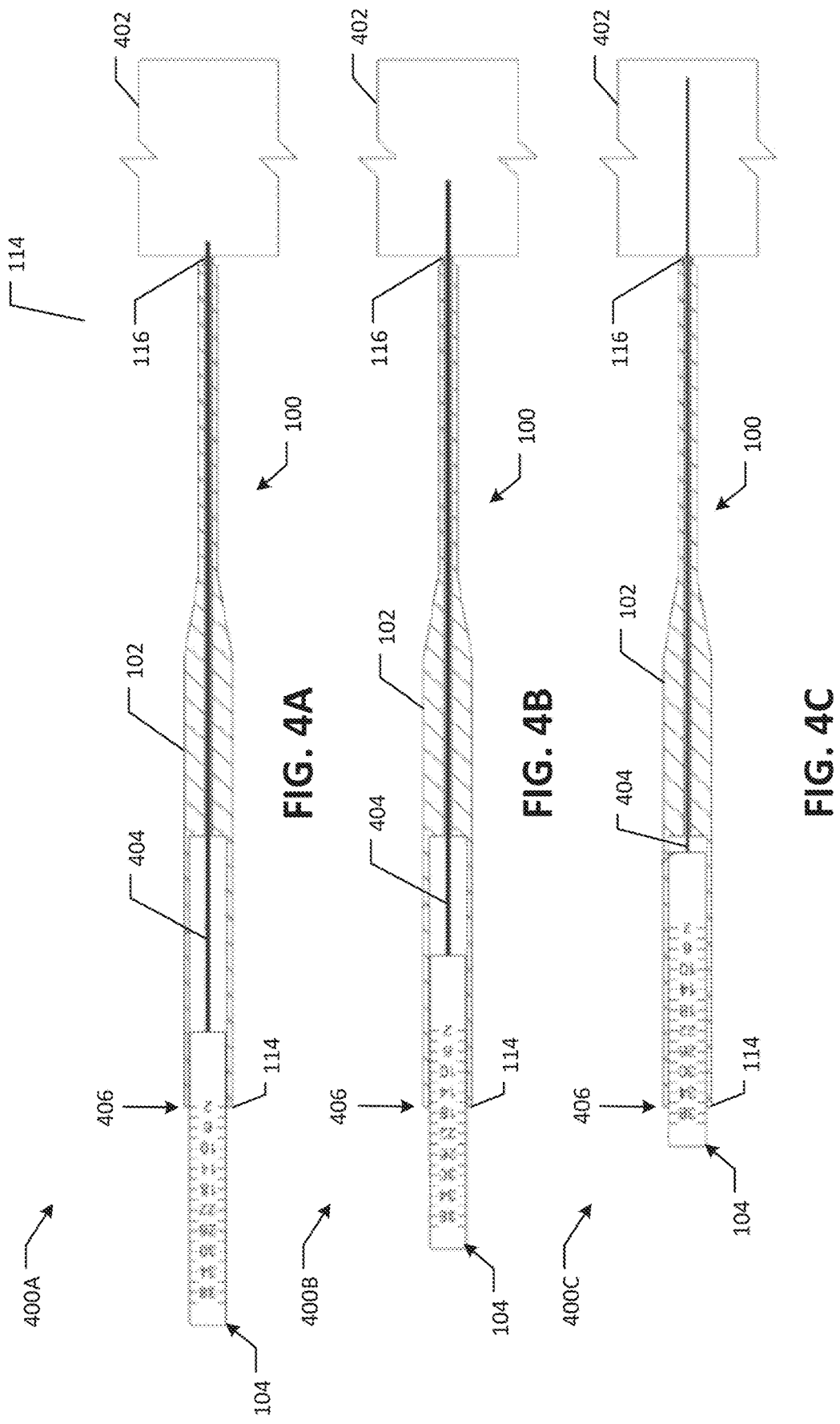

CANNULATED SCREW LENGTH MEASUREMENT GAUGE

PRIORITY CLAIM

The present application claims priority to and the benefit of U.S. Provisional Application 63/086,773, filed Oct. 2, 2020, the entirety of which is herein incorporated by reference.

BACKGROUND

Surgical procedures often involve inserting screws into bone. Surgeons typically insert cannulated screws over guidewires that are first inserted into the bone. The guidewire length is known and the guidewire tip is inserted into the bone to a depth at which the screw tip will be positioned. Prior to inserting a screw, surgeons must determine a screw length that the surgeons will use in such procedures by determining the depth that the guidewire is inserted into the bone.

One way to determine screw length is a device that is placed over or next to a guidewire such that the device contacts bone. With some typical devices, a measurement is taken by determining a location of the end of the guidewire with respect to a scale on the device to determine a length of the guidewire that is external to the bone. This external length may be subtracted from the known total guidewire length to determine the guidewire length inserted within the bone, which is equal to the screw length. In other typical devices, a measurement is taken by determining a location of a laser marking on the guidewire with respect to a scale on the device. The laser marking indicates a specific length, calibrated to the typical measurement device, that helps determine a length of guidewire that is inserted within the bone.

Such typical devices, however, have a number of drawbacks. Further calculations may be required after obtaining a measurement in order to determine a guidewire length that is inserted within the bone, which adds time to a surgical procedure and introduces the possibility of errors in calculation. Often typical devices and guidewires are different for different-sized screws, thus potentially requiring multiple devices for a single surgical procedure. Additionally, the measurement must typically be taken while the device is positioned against bone. Stated differently, once a device is removed from the bone, the device typically no longer displays a measurement because the guidewire end or laser marking are no longer properly lined up on the scale.

Having to take a measurement while the device is positioned against bone may be cumbersome for surgeons if the surgeon has to adjust (e.g., rotate) the measurement device or the surgeon's sightline in order to read a measurement. For example, it may be difficult for a surgeon to see laser markings on a guidewire during a surgical procedure to take a measurement while the markings are very close to the patient and open surgical site because the device must be placed against bone. Surgical time and the procedural difficulty may therefore be increased.

Accordingly, a need exists for a screw length measurement device and method that solve the above-described drawbacks.

SUMMARY

The present disclosure provides new and innovative devices and methods for measuring guidewire depth inserted in bone to determine screw length. In an example, a screw length measurement gauge includes a tube and a measurement rod. The tube includes a guidewire channel and a measurement rod channel. The measurement rod channel has a greater cross sectional area than the guidewire channel. The measurement rod is adjustably positioned within the measurement rod channel. The measurement rod also includes a plurality of indicators along its length. An interface between the tube and the measurement rod maintains a set positioning of the measurement rod in the absence of applied force.

In an example, a screw length determination system includes a guidewire and a depth gauge device. The depth gauge device includes a tube and a measurement rod. The tube includes a guidewire channel and a measurement rod channel. The guidewire channel is configured to receive the guidewire. The measurement rod channel has a greater cross sectional area than the guidewire channel. The measurement rod is positioned within the measurement rod channel. A positioning of the measurement rod is adjustable in response to applied force via the guidewire. The measurement rod also includes a plurality of indicators along its length. An interface between the tube and the measurement rod maintains a set positioning of the measurement rod in the absence of applied force.

In an example, a method for determining a screw length utilizes a depth gauge device including a tube having a guidewire channel and a measurement rod channel, the measurement rod channel having a greater cross sectional area than the guidewire channel, and a measurement rod adjustably positioned within the measurement rod channel, the measurement rod including a plurality of indicators along its length, wherein an interface between the measurement rod channel and the measurement rod maintains a set positioning of the measurement rod in the absence of applied force. The method includes inserting a guidewire into a bone to a desired depth. The depth gauge device is positioned over the guidewire such that the guidewire is inserted within the guidewire channel. The depth gauge device is translated over the guidewire until the depth gauge device contacts the bone. Translating the depth gauge device causes applied force via the guidewire to force a portion of the measurement rod out of the measurement rod channel. The depth gauge device is removed from the bone. A screw length is determined by observing a value of one of the measurement rod indicators, which is equal to the desired depth of the guidewire in the bone.

BRIEF DESCRIPTION OF THE DRAWINGS

FIGS. 4A to 4C illustrate partial cross sections of guidewire depth measurements being taken via a depth gauge device, according to an aspect of the present disclosure.

DETAILED DESCRIPTION

The present disclosure provides new and innovative devices and methods for measuring guidewire depth in bone to determine a screw length needed for a surgical procedure. The provided depth gauge device includes a tube with an interior channel that extends the tube's entire length. The interior channel may be separated into two separate portions that have different-sized cross sectional areas. A measurement rod is inserted into one end of the tube. For instance, the measurement rod may be inserted into the tube's end that has an interior channel with a larger cross sectional area than the other end. In such instances, the other end's interior channel has a smaller cross-sectional area sized to guide and maintain the axial alignment of a guidewire. The measurement rod includes a set of indicators (e.g., lines, indentations, etc.) that are associated with length values (e.g., millimeters). The length values are set corresponding to a known guidewire length.

A surgeon may position the provided depth gauge device over a guidewire, such that the guidewire is inserted into the other end of the tube than the measurement rod. The surgeon may then translate the depth gauge device over the guidewire until the depth gauge device contacts a bone. As the depth gauge device is translated, the guidewire forces the measurement rod partially out of the tube. Once the depth gauge device contacts bone, the indicator on the measurement rod that lines up with a designated spot on the tube indicates a depth that the guidewire is inserted into the bone. This measured depth is equal to a screw length that is needed for the procedure. Accordingly, the provided depth gauge device helps make the screw length determination process easier and faster than some typical devices since the read measurement on the provided depth gauge device is equal to the screw length. No further calculations are necessary as compared to some typical devices.

Additionally, the provided depth gauge device is constructed such that the measurement rod maintains its positioning in the absence of applied force. Stated differently, the measurement rod does not slide into or out of the tube due to gravity. Rather, a guidewire or a surgeon must apply force to the measurement rod in order to force it out of or into the tube. This aspect of the provided depth gauge device enables a surgeon to remove the depth gauge device from the bone or completely from the guidewire when obtaining a measurement reading since the measurement rod will not reposition when the surgeon does so. This aspect helps make it easier and more convenient for a surgeon to see the indicators on the depth gauge device when taking a measurement as compared to typical devices that require the typical device to be positioned against bone when the measurement reading is taken. Accordingly, the provided depth gauge device helps decrease the difficulty and time of screw length determinations in a surgical procedure.

Figure 1:
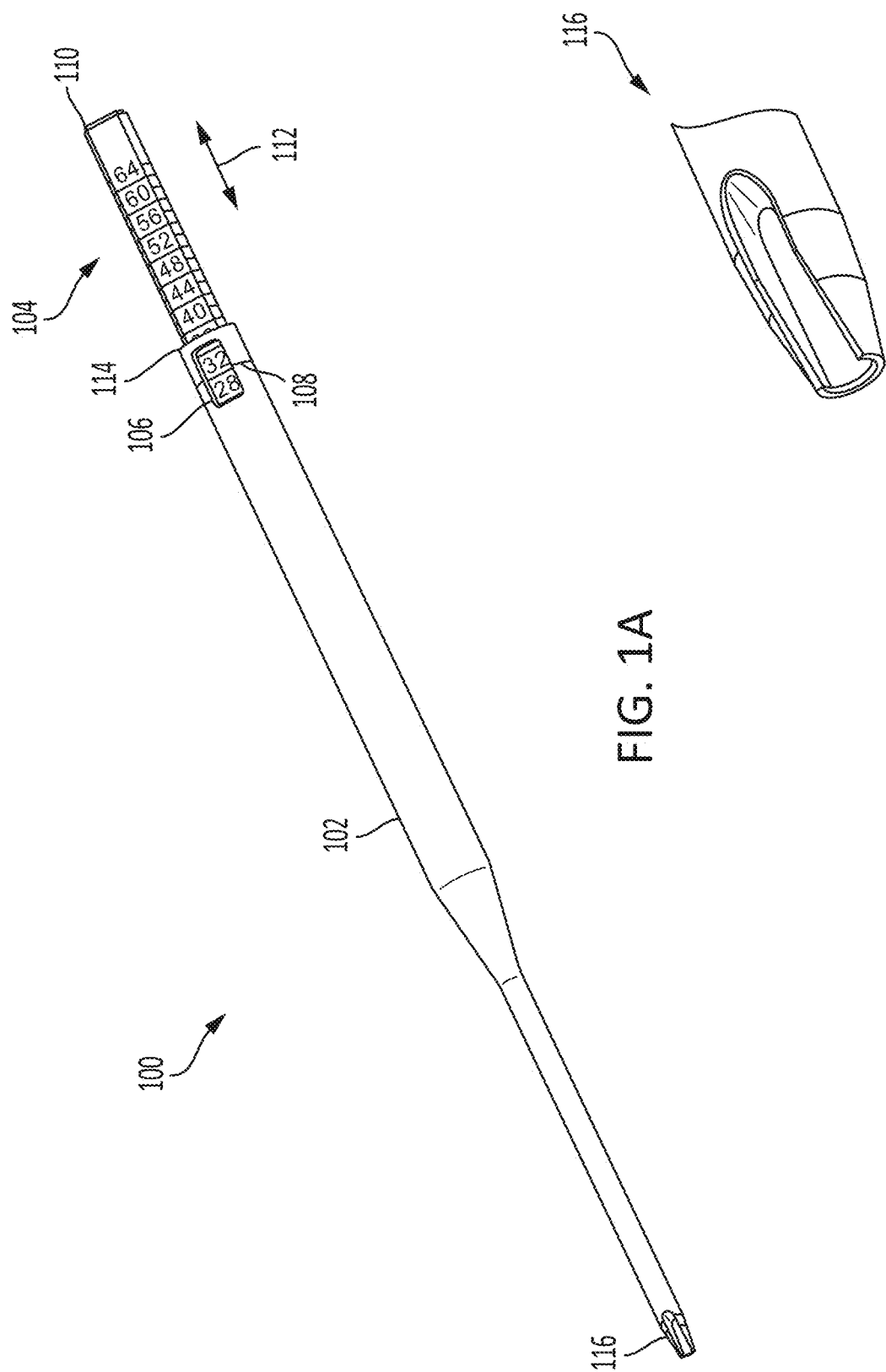
FIG. 1 illustrates a perspective view of a depth gauge device, according to an aspect of the present disclosure.

FIG. 1 illustrates an example depth gauge device 100 having a tube 102 and a measurement rod 104. The tube 102 may be constructed from any suitable medical-grade material, such as stainless steel or a medical-grade plastic (e.g., polyether ether ketone). The measurement rod 104 may be constructed from any suitable medical-grade material that is also suitably rigid, such as aluminum or a medical-grade plastic (e.g., polyether ether ketone). The measurement rod 104 may be adjustably positioned into and out of the tube 102 in the direction of the double-side arrow 112. In some instances, a distal end 110 of the measurement rod 104 may be positioned fully within the tube 102. As illustrated, the measurement rod 104 includes a plurality of indicators (e.g., lines or tick marks, indentations, etc.) that are associated with a length value (e.g., millimeters, centimeters, etc.). The associated length values are selected to correspond to a specific guidewire length. At least some of the indicators may have their associated value or quantity visually indicated (e.g., printed, etched, etc.) on the measurement rod. For example, in the illustrated embodiment, every other indicator has its associated value visually indicated.

In some aspects of the present disclosure, such as the illustrated example, the tube 102 may include a window 106. The window 106 enables a surgeon to see an indicator on the measurement rod 104 through the window 106. In some instances, the tube 102 may include one or more markings 108 (e.g., a laser marking) next to the window 106. The illustrated example tube 102 includes a marking 108 on either side of the window 106, though in other instances, the tube 102 may include a marking 108 on only one side. The marking 108 signals to a surgeon which indicator on the measurement rod 104 should be taken as the measurement (e.g., the value of the indicator that lines up with the marking 108). In other instances, the tube 102 may, additionally or alternatively, include one or more notches that extend into the interior of the window 106 to signal which indicator should be taken as the measurement (e.g., the value of the indicator that lines up with the notch).

In other aspects of the present disclosure, the tube 102 does not include a window 106. Instead, a surgeon relies upon seeing the indicators as they exit the tube 102. In such aspects, a measurement end 114 of the tube 102 signals to a surgeon which indicator on the measurement rod 104 should be taken as the measurement (e.g., the value of the indicator that lines up with the measurement end 114).

The tube 102 additionally includes an insertion end 116. As described in more detail below, a surgeon may translate the depth gauge device 100 over a guidewire with the guidewire entering the tube 102 at its insertion end 116. The insertion end 116 may be particularly adapted to help engage a guidewire. For instance, FIG. 1B illustrates an example of one such particular adaptation of the insertion end 116. The slot opening of the insertion end 116 that extends along a portion of the tube 102 allows extra space for the guidewire to enter the tube 102. This extra space makes it easier to align the small guidewire with the small opening of the insertion end 116 as compared to a simple round opening at the end of the tube 102 by enabling the guidewire to be side-loaded into the tube 102.

Figure 2:
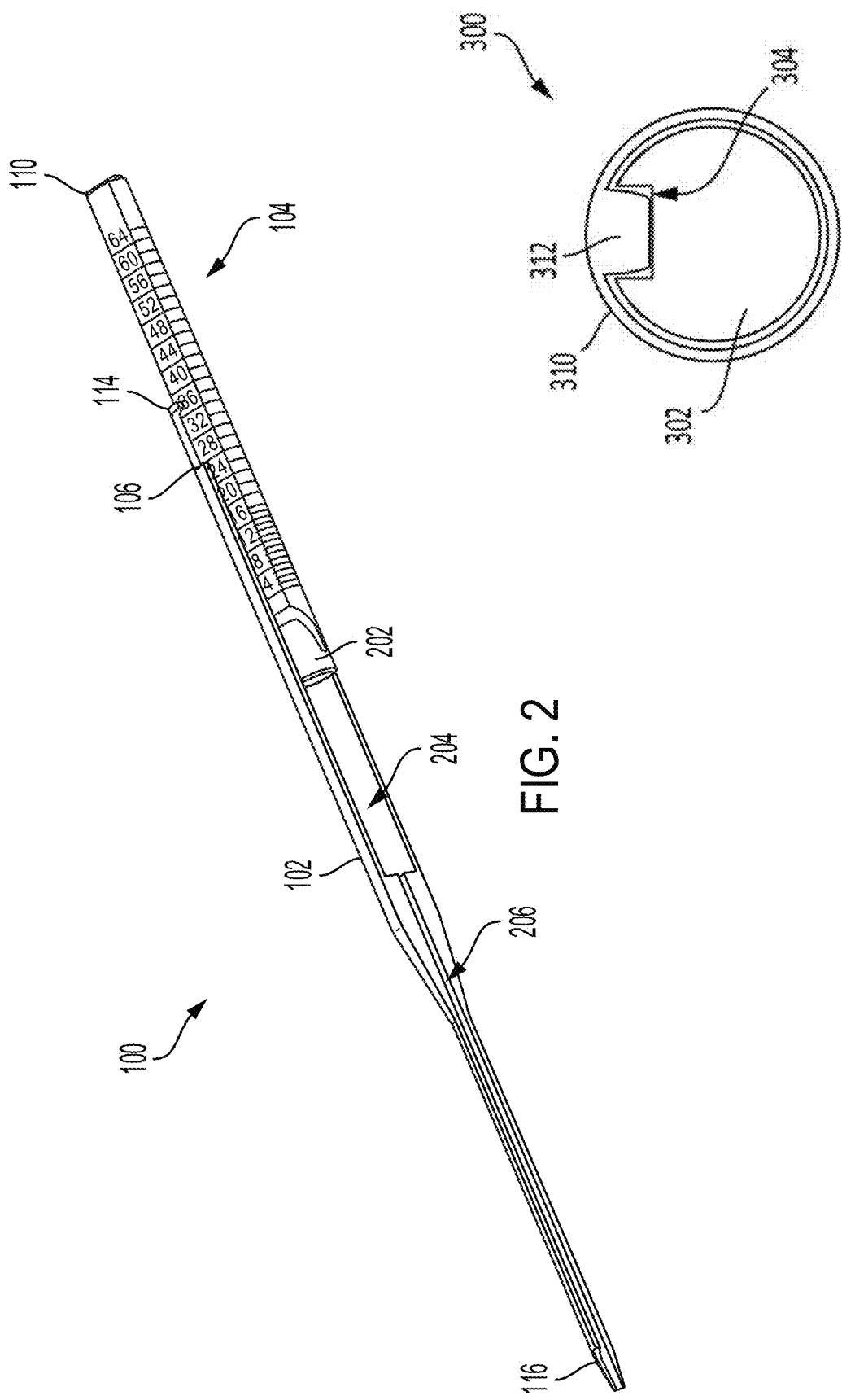
FIG. 2 illustrates a partial cross section of a depth gauge device, according to an aspect of the present disclosure.

FIG. 2 illustrates the example depth gauge device 100 with a cross section of the tube 102 to show the internal channel(s) of the tube 102. Specifically, the tube 102 may include a measurement rod channel 204. The measurement rod channel 204 maintains axial alignment of the measurement rod 104. The measurement rod channel 204 also enables the measurement rod 104 to be slid into and out of the measurement rod channel 204. The tube 102 may also include a guidewire channel 206. In various instances, a guidewire has a smaller cross sectional area than the measurement rod 104. In such instances, the guidewire channel 206 may have a smaller cross sectional area (e.g., minimally larger than the guidewire's cross sectional area) than the measurement rod channel 204 so that the guidewire channel 206 may better maintain axial alignment of the guidewire as compared to a single channel with a cross sectional area of the measurement rod channel 204.

For example, as described in more detail below, a guidewire inserted within the tube 102 applies force to a proximal end 202 of the measurement rod 104 to force the measurement rod 104 out of the tube 102. Such force may translate into causing the guidewire to bend if a sufficient length of guidewire has space to bend within the tube 102. If the guidewire bends, the length measurement may be compromised. The guidewire channel 206 may therefore have a cross sectional area that is minimally larger than the guidewire's cross sectional area to help maintain axial alignment of the guidewire and help prevent guidewire bending. In some examples, the guidewire channel 206 may have a cross sectional area that accommodates guidewires having the same length, but different cross sectional area sizes. In such examples, guidewires with smaller cross sectional areas will have more space between the guidewire and the walls of the guidewire channel 206, though to a degree that bending is minimized and length measurement are not compromised.

In instances in which the tube 102 includes both a measurement rod channel 204 and a guidewire channel 206, the measurement rod channel 204 and the guidewire channel 206 may span various portions of the length of the tube 102. The difference in cross sectional areas between the guidewire channel 206 and the measurement rod channel 204 additionally establishes a stopping point for the measurement rod 104, past which the measurement rod 104 may not travel. In some aspects, the cross sectional area of the measurement rod 104 may be equal to or about the guidewire s cross sectional area. In such aspects, the tube 102 may include a single, continuous channel that extends its length.

In some aspects of the present disclosure, the measurement rod 104 may include at least one flat surface along its length. For instance, the measurement rod 104 is illustrated as having a flat surface including the visually indicated values. The one or more flat surface of the measurement rod 104 prevents the measurement rod 104 from rotating in conjunction with a flat surface on the interior of the tube 102. This may be beneficial by helping prevent a surgeon from having to rotate the measurement rod 104 during a procedure in order to see the visually indicated measurement values. The exterior of the tube 102 may, additionally or alternatively, include at least one flat surface to help prevent the depth gauge device 100 from rolling. This may be beneficial because it may help prevent the depth gauge device 100 from rolling off a surface onto the floor.

Figure 3:
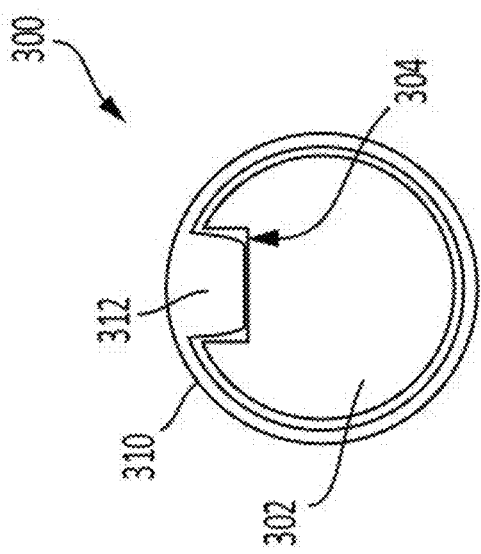
FIG. 3 illustrates a cross section of a depth gauge device having a notch and key, according to an aspect of the present disclosure.

In other aspects of the present disclosure, the measurement rod 104 may be cylindrical. In such aspects, the depth gauge device 100 may include a notch and key to prevent the measurement rod 104 from rotating. FIG. 3 illustrates a cross section of an example depth gauge device 300 including a measurement rod 302 having a notch 304 and a tube 310 having a key 312. The key 312 is attached to or integral with an interior surface of the tube 310. The key 312 is shaped to fit within the notch 304 of the measurement rod 302 as illustrated. The amount of space between the key 312 and the sides of the notch 304 determines how much the measurement rod 302 is able to rotate before being stopped by the key 312. Accordingly, the key 312 helps minimize rotation or prevents the measurement rod 302 from rotating when the measurement rod 302 is positioned within the tube 310.

FIGS. 4A to 4C illustrate example guidewire depth measurements being taken via the depth gauge device 100. In each of the figures, a cross section of the tube 102 is illustrated to show the interior of the depth gauge device 100. FIG. 4A illustrates an example measurement 400A. The guidewire 404 is inserted a certain depth into the bone 402. The depth gauge device 100 is positioned over the guidewire 404 such that the insertion end 116 contacts the bone 402. The guidewire 404 has forced the measurement rod 104 out of the tube 102 to a certain degree. In the example measurement 400A, a surgeon may read that the indicator on the measurement rod 104 corresponding to 2 mm lines up with the measurement end 114 of the tube 102. Accordingly, the guidewire 404 is inserted to a depth of 2 mm into the bone 402 in the measurement 402.

FIG. 4B illustrates an example measurement 400B. As illustrated, the guidewire 404 is inserted to a greater depth into the bone 402 than in the measurement 400A. In the measurement 400B, the guidewire 404 has therefore forced the measurement rod 104 out of the tube 102 to a lesser degree than in the measurement 400A. In the example measurement 400B, a surgeon may read that in between the 16 mm indicator and the 18*mm* indicator on the measurement rod 104 lines up with the measurement end 114 of the tube 102. Accordingly, the guidewire 404 is inserted to a depth of 17 mm into the bone 402 in the measurement 400B.

FIG. 4C illustrates an example measurement 400C. As illustrated, the guidewire 404 is inserted to a greater depth into the bone 402 than in both the measurements 400A and 400B. In the measurement 400C, the guidewire 404 has therefore forced the measurement rod 104 out of the tube 102 to a lesser degree than in the measurements 400A and 400B. In the example measurement 400C, a surgeon may read that in between the 36 mm indicator and the 38*mm* indicator on the measurement rod 104 lines up with the measurement end 114 of the tube 102. Accordingly, the guidewire 404 is inserted to a depth of 37 mm into the bone 402 in the measurement 400C.

The presently disclosed depth gauge device is constructed such that the measurement rod maintains its positioning relative to the tube in the absence of an applied force. For example, in the measurement 400C, applied force from the guidewire 404 forced the measurement rod 104 out of the tube 102. When a surgeon removes the depth gauge device 100 from the guidewire 404, however, the measurement rod 104 maintains the 37 mm reading. Gravity does not cause the measurement rod 104 to slide back into or out of the tube 102. A surgeon may apply force to the measurement rod 104 to force the measurement rod 104 back into the tube 102. The provided depth gauge device may have various constructions such that an interface between the measurement rod and the tube enable the measurement rod to maintain its positioning in the absence of applied force.

Figure 5A:
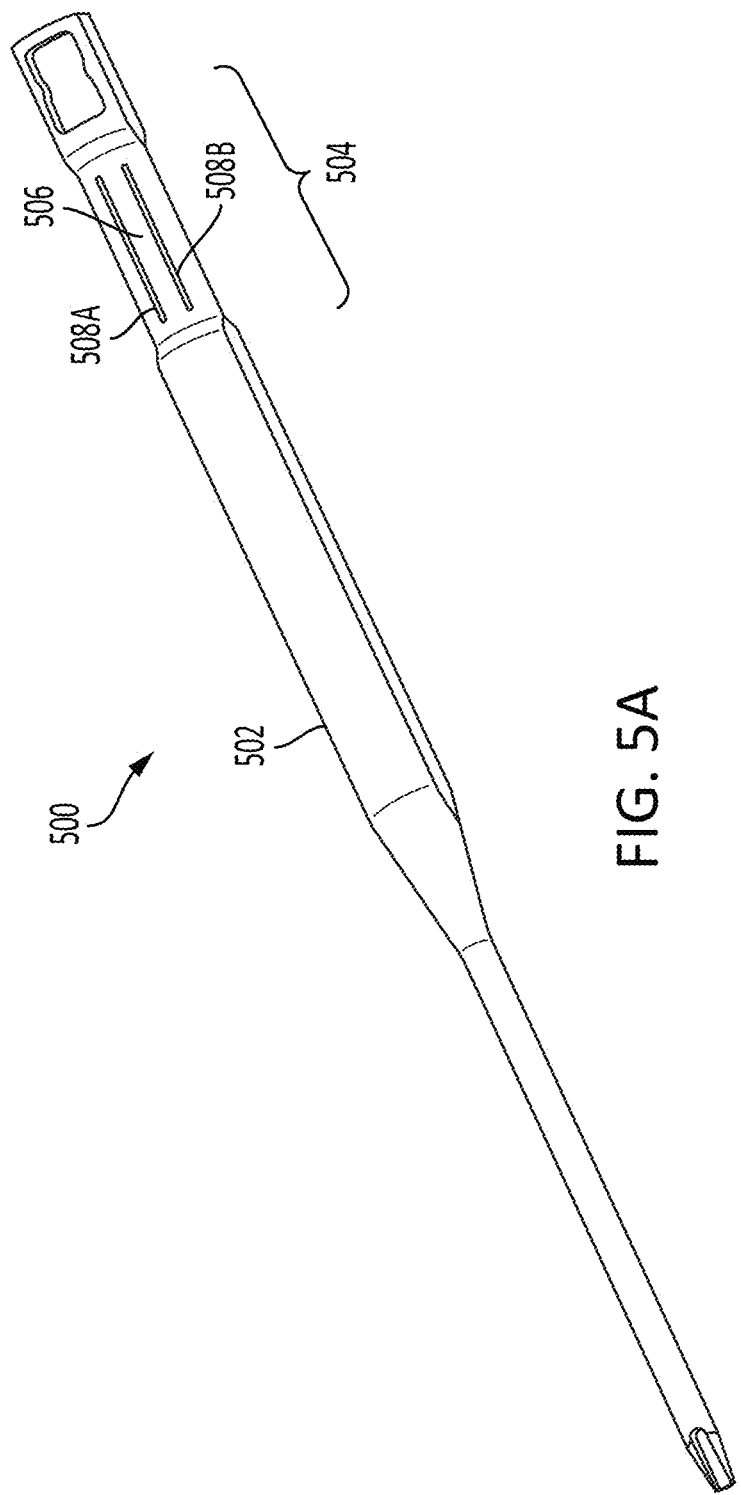
FIG. 5A illustrates a perspective view of a depth gauge device having a friction spring, according to an aspect of the present disclosure.
Figure 5B:
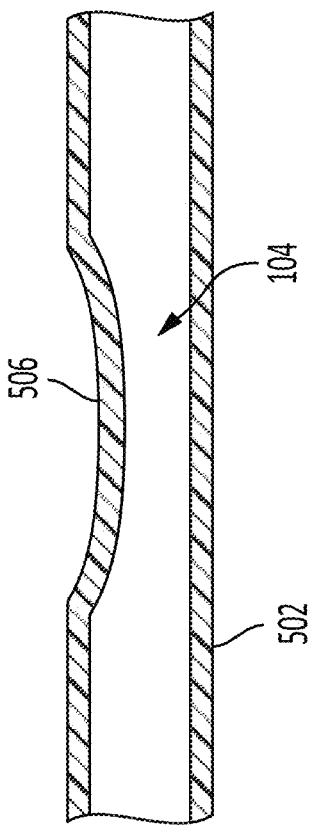
FIG. 5B illustrates a cross section of a portion of a depth gauge device having a friction spring, according to an aspect of the present disclosure.

FIG. 5A illustrates a perspective view of an example depth gauge device 500 having a friction spring 506 for maintaining a position of the measurement rod 104. A portion 504 of the tube 502 of the depth gauge device 500 includes two slits 508A, 508B that separate the friction spring 506 from the rest of the tube 502. FIG. 5B illustrates a cross section of the portion 504 with a measurement rod 104 inserted within the tube. The friction spring 506 is biased towards the interior of the tube 502. In this way, the friction spring 506 applies inward force to the measurement rod 104, generating friction at the interface between the friction spring 506 and the measurement rod 104. The generated friction is sufficient to maintain the measurement rod 506 in its position in the absence of applied force, but can be overcome by applied force to the measurement rod 506 (e.g., via a guidewire or a surgeon). The amount of friction generated, and therefore the amount of applied force required to move the measurement rod 104, can be altered based on the strength of the friction spring 506.

Figure 6:
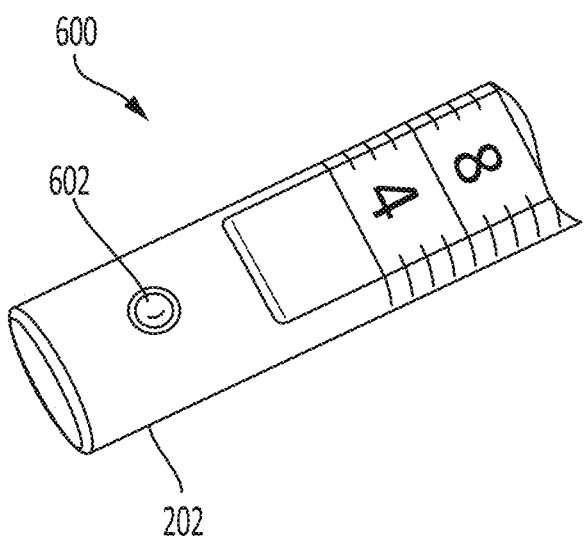
FIG. 6 illustrates a perspective view of a portion of a measurement rod having a spring and ball plunger, according to an aspect of the present disclosure.

In another example, the provided depth gauge device may include a spring and ball plunger to maintain the positioning of the measurement rod in the absence of applied force. FIG. 6 illustrates a proximal end 202 of an example measurement rod 600 having a spring and ball plunger 602. The spring and ball plunger 602 applies outward force to the interior of the tube (e.g., the tube 102) when positioned within the tube, which generates friction at the interface between the spring and ball plunger 602 and the tube interior. The generated friction is sufficient to maintain the measurement rod 600 in its position in the absence of applied force, but can be overcome by applied force to the measurement rod 600 (e.g., via a guidewire or a surgeon). The amount of friction generated, and therefore the amount of applied force required to move the measurement rod 600, can be altered based on the strength of the spring and ball plunger 602. In other examples, the tube may include the spring and ball plunger 602, which may apply inward force to the measurement rod to generate friction.

Figure 7:
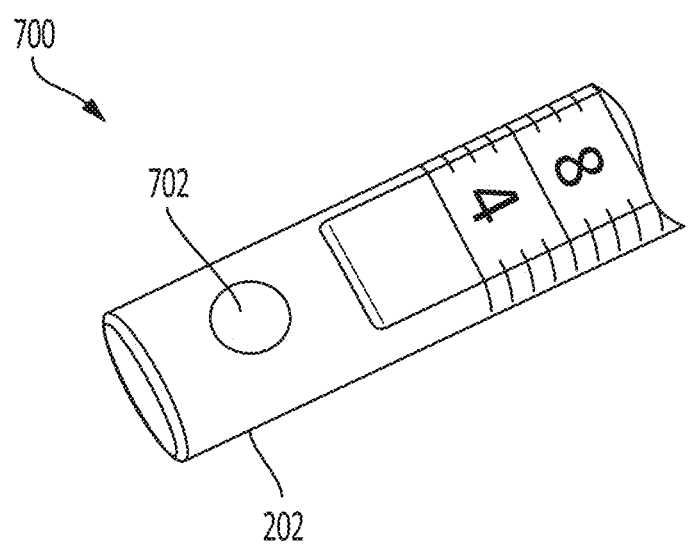
FIG. 7 illustrates a perspective view of a portion of a measurement rod having a magnet, according to an aspect of the present disclosure.

In another example, the provided depth gauge device may include a set of magnets to maintain the positioning of the measurement rod in the absence of applied force. FIG. 7 illustrates a proximal end 202 of an example measurement rod 700 having a magnet 702. The magnet 702 has a first polarity (e.g., north). In some examples, the interior of the depth gauge device's tube includes a second magnet having the opposite polarity (e.g., south). The polarities of these two magnets may be flipped. In such examples, the tube's magnet extends the length of the measurement rod channel. The magnet 702 is attracted to the tube's magnet by magnetic force when the measurement rod 700 is positioned within the tube. The magnetic force at the interface between the magnet 702 and the tube's magnet is sufficient to maintain the measurement rod 700 in its position in the absence of applied force, but can be overcome by applied force to the measurement rod 700 (e.g., via a guidewire or a surgeon). The amount of magnetic force, and therefore the amount of applied force required to move the measurement rod 700, can be altered based on the strength of the magnet 702 and the strength of the tube's magnet.

In other examples, the magnet 702 may extend the length of the measurement rod 700 (e.g., along its side or bottom). In such other examples, the tube's interior magnet may be a single point (e.g., the magnet 702 as illustrated). In other examples still, the depth gauge device's tube may be constructed of a magnetic material (e.g., stainless steel) such that the magnet 702 of the measurement rod 700 is attracted to the tube itself rather than a magnet constructed as part of the tube.

The magnet 702 and the tube or the tube's interior magnet may be any material of suitable magnetic strength to maintain the positioning of the measurement rod 700 in the absence of applied force, but that can be overcome by applied force via a guidewire or a surgeon. For example, the magnet 702 and the tube's interior magnet may be a neodymium magnet or a samarium-cobalt magnet. As described above, the tube itself may be constructed of a magnetic stainless steel in certain instances. The magnet 702 and the tube or the tube's interior magnet may have, for example, a magnetic pull strength of about 0.3 lbs to 1.0 lbs.

Figure 8A:
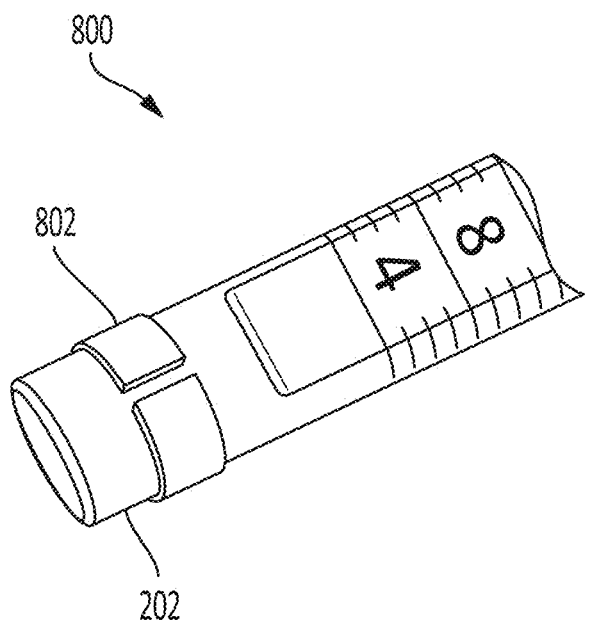
FIG. 8A illustrates a perspective view of a portion of measurement rod having a ring spring, according to an aspect of the present disclosure.
Figure 8B:
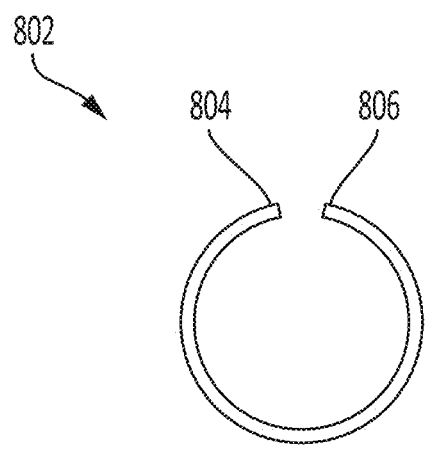
FIG. 8B illustrates a cross section of a ring spring, according to an aspect of the present disclosure.

In another example, the provided depth gauge device may include a ring spring to maintain the positioning of the measurement rod in the absence of applied force. FIG. 8A illustrates a proximal end 202 of an example measurement rod 800 having a ring spring 802. The ring spring 802 applies outward force to the interior of the tube (e.g., the tube 102) when positioned within the tube, which generates friction at the interface between the ring spring 802 and the tube interior. For example, FIG. 8B illustrates a cross section of the ring spring 802. The ring spring 802 is constructed such that it is biased to maintain the illustrated positioning, but the ends 804 and 806 may be forced towards one another to reduce the diameter of the ring spring 802. To insert the measurement rod 800 into the tube, the ends 804 and 806 must be forced towards one another so that the ring spring 802 is constrained within the tube. Once inserted, the ring spring 802 is biased to return to its resting shape so it applies outward force to the interior of the tube.

The generated friction at the interface between the ring spring 802 and the tube interior is sufficient to maintain the measurement rod 800 in its position in the absence of applied force, but can be overcome by applied force to the measurement rod 800 (e.g., via a guidewire or a surgeon). The amount of friction generated, and therefore the amount of applied force required to move the measurement rod 800, can be altered based on the strength of the ring spring 802.

Figure 9:
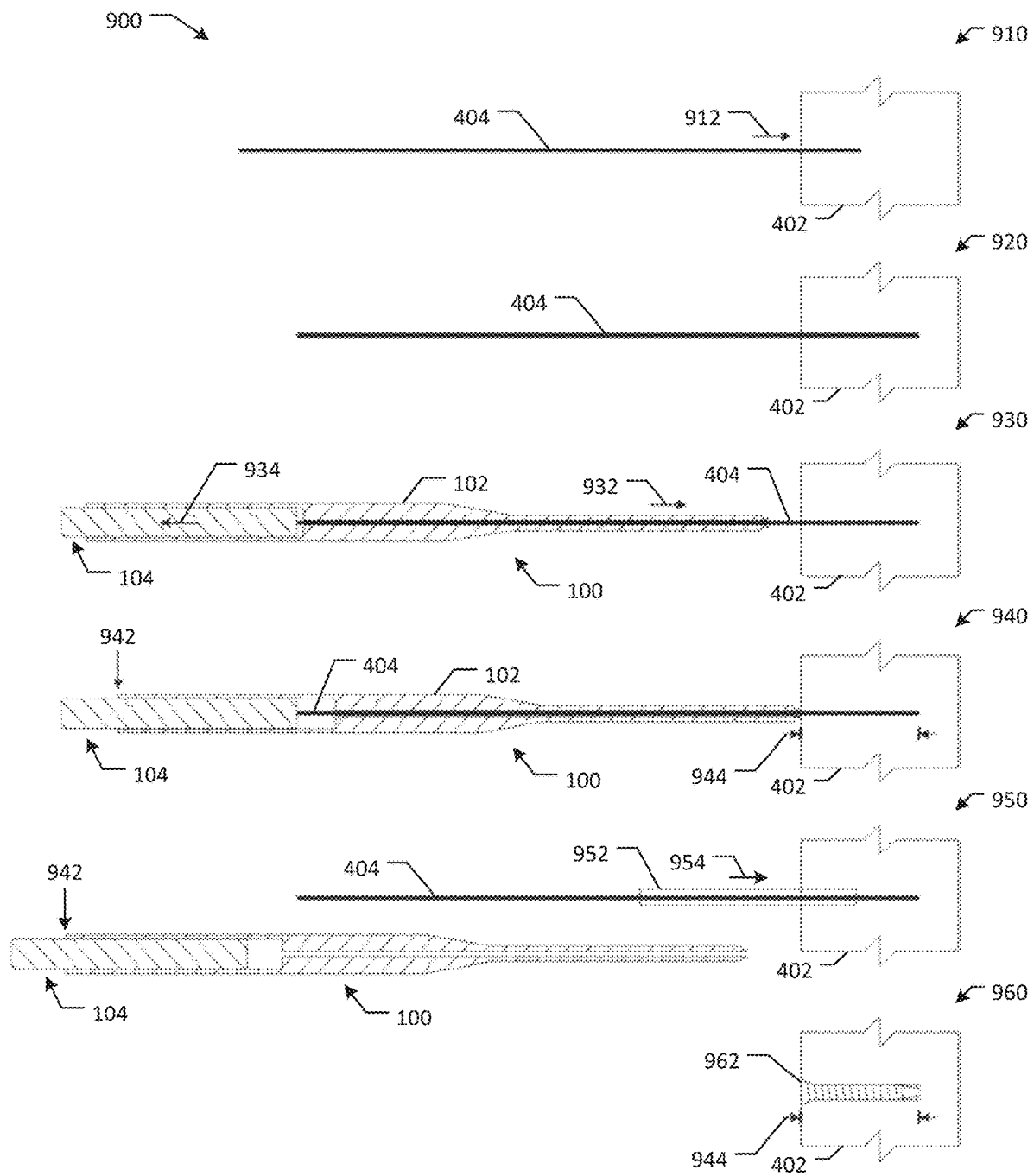
FIG. 9 illustrates cross sections of method steps for a screw length determination method, according to an aspect of the present disclosure.

FIG. 9 illustrates an example method 900 for determining a screw length to be used in a surgical procedure. Although the example method 900 is described with reference to the illustrations shown in FIG. 9, it will be appreciated that many other methods of performing the acts associated with the method 900 may be used. For example, certain steps may be combined with other steps and some steps may be performed that are not illustrated. Additionally, the example method 900 may be performed with any of the described examples of the provided depth measuring device.

A guidewire 404 may be inserted into bone 402 in the direction of the arrow 912 (step 910). For example, the guidewire 404 may be drilled into the bone 402. The guidewire 404 is inserted until a desired depth into the bone 402 is reached (step 920). After the desired depth is reached, a depth measuring device (e.g., the depth measuring device 100) is positioned over the guidewire 404 such that the guidewire 404 is within the tube 102 of the depth measuring device 100. The depth measuring device 100 is then translated over the guidewire 404 towards the bone 402 in the direction of the arrow 932 (step 930). At some point while the depth measuring device 100 is translated over the guidewire 404, the guidewire 404 first contacts the measurement rod 104. From this point on, as the depth measuring device 100 is further translated towards the bone 402, the applied force from the guidewire 404 forces the measurement rod 104 out of the tube 102 in the direction of the arrow 934.

Once the depth measuring device 100 contacts the bone 402, a measurement reading may be taken (step 940). To take the measurement reading, the surgeon may read a length value 942 (e.g., 20 mm) corresponding to an indicator on the measurement rod 104 that lines up with a measurement end of the tube 102. The length value 942 corresponds to a depth 944 (shown by the opposing arrows) of the guidewire 404 into the bone 402. Accordingly, the length value 942 also corresponds to a screw length needed for the procedure. In some instances, a surgeon may take the measurement reading while the depth gauge device 100 is still contacting the bone 402, or is otherwise still positioned over the guidewire 404, as illustrated at step 940. In other instances, the surgeon may remove the depth gauge device 100 from the guidewire 404 and take the measurement reading (e.g., as shown in step 950 in which the depth gauge device 100 is removed from the guidewire 404 and still shows the length value 942 as the measurement reading). In such other instances, it may be easier for the surgeon to see the measurement reading when the depth gauge device 100 is away from the patient.

A cannulated drill 952 may be translated over the guidewire 404 in the direction of the arrow 954 and into the bone 402 (step 950). A surgeon may use the cannulated drill 952 to drill a hole to the depth 944 equal to the length value 942, or to an otherwise desired depth. The cannulated drill 952 is then removed from the bone 402. A cannulated screw 962 having a length 944 (shown by the opposing arrows) equal to the length value 942 may then be driven into the bone 402 over the guidewire 404 (step 960). For instance, a surgeon may use a hand held driver handle or power driver to drive the cannulated screw 962 into the bone 402. Once the cannulated screw 962 is fully inserted, the guidewire 404 is then removed. Accordingly, a surgeon may quickly and easily determine a screw length needed for a surgical procedure and may insert a screw having such length.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A screw length determination system comprising:
a set of guidewires; and
a depth gauge device including:
   a tube having (i) a guidewire channel configured to receive the set of guidewires and (ii) a measurement rod channel, the measurement rod channel having a greater cross sectional area than the guidewire channel; and
   a measurement rod positioned within the measurement rod channel, wherein a positioning of the measurement rod is adjustable in response to applied force via the guidewires, and wherein the measurement rod includes a plurality of indicators along its length,
   wherein an interface between the measurement rod channel and the measurement rod maintains a set positioning of the measurement rod in the absence of applied force, wherein each guidewire in the set has a different size diameter,
wherein the guidewire channel is sized to accommodate each of the guidewires in the set.

2. The screw length determination system of claim 1, further comprising a cannulated drill.

3. The screw length determination system of claim 1, wherein the measurement rod includes a notch and the tube includes a protrusion within the measurement rod channel, the protrusion positioned within the notch.

4. The screw length determination system of claim 1, wherein the tube includes a friction spring and the interface includes the friction spring contacting the measurement rod.

5. The screw length determination system of claim 1, wherein the depth gauge device further comprises a spring and ball plunger and the interface includes the spring and ball plunger contacting the measurement rod or the tube.

6. The screw length determination system of claim 1, wherein the measurement rod includes a first magnetic material having a first polarity and the tube includes a second magnetic material having the opposite polarity of the first magnetic material, and wherein the interface includes the first magnetic material contacting the second magnetic material.

7. The screw length determination system of claim 1, wherein the measurement rod includes a ring spring and the interface includes the ring spring contacting the tube.

* * * * *